US009289499B2

United States Patent
Van Den Broek et al.

(10) Patent No.: US 9,289,499 B2
(45) Date of Patent: Mar. 22, 2016

(54) CONTINUOUS FLOW PRODUCTION OF GELATIN NANOPARTICLES

(75) Inventors: Sebastiaan Antonius Martinus Waltherus Van Den Broek, Nijmegen (NL); Pieter Jos Nieuwland, Nijmegen (NL); Kaspar Koch, Nijmegen (NL)

(73) Assignee: FUTURECHEMISTRY HOLDING B.V., Nijmegen (NL)

( * ) Notice: Subject to any disclaimer, the term of this patent is extended or adjusted under 35 U.S.C. 154(b) by 0 days.

(21) Appl. No.: 14/128,150

(22) PCT Filed: Jul. 2, 2012

(86) PCT No.: PCT/EP2012/002770
§ 371 (c)(1),
(2), (4) Date: Dec. 20, 2013

(87) PCT Pub. No.: WO2013/004370
PCT Pub. Date: Jan. 10, 2013

(65) Prior Publication Data
US 2014/0179803 A1    Jun. 26, 2014

(30) Foreign Application Priority Data
Jul. 1, 2011   (EP) ..................................... 11005386

(51) Int. Cl.
| A61K 47/42 | (2006.01) |
| A61K 9/51 | (2006.01) |
| B82Y 5/00 | (2011.01) |
| A61K 9/14 | (2006.01) |

(52) U.S. Cl.
CPC .............. *A61K 47/42* (2013.01); *A61K 9/146* (2013.01); *A61K 9/5169* (2013.01); *A61K 9/5192* (2013.01); *B82Y 5/00* (2013.01)

(58) Field of Classification Search
None
See application file for complete search history.

(56) References Cited

U.S. PATENT DOCUMENTS

| 5,560,924 A | 10/1996 | Wunderlich et al. |
| 5,932,245 A | 8/1999 | Wunderlich et al. |
| 6,391,452 B1 * | 5/2002 | Antonsen ............. A61K 9/0043 264/4.1 |
| 2005/0220915 A1 | 10/2005 | Nakamura et al. |
| 2006/0087048 A1 * | 4/2006 | Mello et al. ...................... 264/11 |
| 2008/0003292 A1 * | 1/2008 | Ahlers et al. .................. 424/489 |
| 2010/0209519 A1 | 8/2010 | Lin et al. |
| 2012/0118105 A1 * | 5/2012 | Irizarry ..................... B22F 9/24 75/371 |

FOREIGN PATENT DOCUMENTS

| CN | 1508154 A | 6/2004 |
| CN | 1988892 A | 6/2007 |
| WO | 2004 076056 A2 | 9/2004 |
| WO | 2005 000265 A2 | 1/2005 |

OTHER PUBLICATIONS

Panić et al., Experimental approaches to a better understanding of mixing performance of microfluidic devices, Chem. Eng. J. 2004, 101(1-3):409-419.*
Suh et al., A Review on Mixing in Microfluidics. Micromachines 2010, 1(3), 82-111.*
Panic, S, et al., Experimental approaches to a better understanding of mixing performance of microfluidic devices, Chemical Engineering Journal, 101, 2004, pp. 409-419.
S. Panic, et al., Experimental Approaches to a Better Understanding of Mixing Performance of Microfluidic Devices, Chemical Engineering Journal 101, 2004, pp. 409-419.
Y. Ying, Preparation of Nano-Materials via Precipitation in Microchannel Reactors, Dissertation of Master's Degree, class of 2004, Laboratory of Chemical Engineering, Dalian Institute of Chemical Physics, Apr. 2007, pp. 1-95, no volume or issue number, Publisher: Dalian Institute of Chemical Physics, Chinese Academy of Sciences.

* cited by examiner

*Primary Examiner* — Robert A Wax
*Assistant Examiner* — Olga V Tcherkasskaya
(74) *Attorney, Agent, or Firm* — Hudak, Shunk & Farine Co. LPA

(57) ABSTRACT

A continuous process for the preparation of gelatin based nanoparticles in a reactor having a process channel having a mixing element therein, the process having the following steps: A) feeding separately an aqueous gelatin solution at a first rate and a water-miscible organic solvent at a second rate to the process channel of the reactor to be mixed therein, to form a suspension of non-crosslinked gelatin based nanoparticles and B) crosslinking the non-crosslinked gelatin based nanoparticles, wherein the sum of the first rate and the second rate is chosen such that the reactor has a mixing efficiency as determined by the Villermaux/Dushman method of between 0.1 and 1.5 and the period from the time point at which the aqueous gelatin solution is fed to the reactor to the time point at which the mixture of the aqueous gelatin solution and the organic solvent contacts the mixing element is at most 15 seconds.

20 Claims, 6 Drawing Sheets

(a)  (b)

CONTINUOUS FLOW PRODUCTION OF GELATIN NANOPARTICLES

FIELD OF THE INVENTION

The present invention relates to a process for the preparation of gelatin based nanoparticles.

BACKGROUND OF THE INVENTION

In recent years, significant effort has been devoted to develop nanotechnology for drug delivery since it offers a suitable means of delivering small molecular weight drugs, as well as macromolecules such as proteins, peptides or genes by either localized or targeted delivery to the tissue of interest. Nanotechnology focuses on formulating therapeutic agents in biocompatible nanocomposites such as nanoparticles, nanocapsules, micellar systems, and conjugates. Protein nanoparticles (BSA, HAS and gelatin) generally vary in size from 20-500 nm and they hold certain advantages such as greater stability during storage, stability in vivo, non-toxicity, non-antigen and ease to scale up during manufacture over the other drug delivery systems. The primary structure of gelatin offers many possibilities for chemical modification and covalent drug attachment, e.g. for drug delivery in general, and as an injectable drug delivery system in particular.

Some fractures heal only slowly due to complexity of the fracture or because the patient has a retarded growth. Current methods to accelerated growth make use of a growth factor bounded to tissue, e.g. collagen. This method activates bone cells to activate growth. Existing methods are based on filling the fracture with granulate material from natural or synthetic resources. This requires invasive surgery, which is demanding for the patient.

Another more preferred option is to use injectable materials. For example, U.S. Pat. No. 5,932,245 discloses a dosage formulation that provides for the release of nanoparticles. It comprises (a) an inner phase that comprises at least one nanoparticle compound; and (b) an outer phase that comprises a compound selected from the group consisting of gelatin, collagen hydrolyzates and mixtures thereof. The preferred nanoparticle size is in the range from 10-800 nm. Glibenclamide is mentioned as the nanoparticle compound for treatment of diabetes.

US 2008/0003292 discloses nanoparticles, essentially consisting of an aqueous gelatin gel, wherein the nanoparticles have an average diameter of at most 350 nm and polydispersity index of less than or equal to 0.15. The nanoparticles are used as carrier systems for medical substances. This publication deals with the problem of broad size distribution of nanoparticles which is disadvantageous with a view to a uniform release and transport behavior. In the examples, gelatin is dissolved in water and pH value is adjusted. The de-solvation of the gelatin is carried out by way of the drop by drop addition of acetone. Aqueous glutaric aldehyde solution is added. The nanoparticles cross-linked in this way are separated from the solution.

The known processes for making gelatin nanoparticles are difficult to control.

SUMMARY OF THE INVENTION

It is an object of the present invention to provide a novel process for making gelatin based nanoparticles which overcomes above and/or other problems.

Accordingly, the present invention provides a continuous process for the preparation of gelatin based nanoparticles in a reactor comprising a process channel comprising a mixing element therein, the process comprising the following steps: A) feeding separately an aqueous gelatin solution at a first rate and a water-miscible organic solvent at a second rate to the process channel of the reactor to be mixed therein, to form a suspension of non-crosslinked gelatin based nanoparticles and B) crosslinking the non-crosslinked gelatin based nanoparticles, wherein the sum of the first rate and the second rate is chosen such that the reactor has a mixing efficiency as determined by the Villermaux/Dushman method of between 0.1 and 1.5 and the period from the time point at which the aqueous gelatin solution is fed to the reactor to the time point at which the mixture of the aqueous gelatin solution and the organic solvent contacts the mixing element is at most 15 seconds.

The inventors have surprisingly found that gelatin based nanoparticles can be made by a continuous process. Preferably the process is carried out in a micro reactor or flow reactor. The continuous process is herein understood to mean a process in which products are continuously extracted and reactants are continuously replenished.

In the prior art batch process, the de-solvation of the gelatin is carried out by way of the drop by drop addition of acetone. In such a process, the concentration of the acetone in the mixture is slowly increased, until a certain point in time at which gelatin nanoparticles start to form. The drop by drop addition is required, since if the acetone is added in one step, phase separation occurs, and large aggregates will be formed in the end. The two phases then slowly mix to a homogeneous solution together with the formation of large aggregates instead of nanoparticles. It was considered in the art that the requirement for the slow increase in the acetone concentration ensured by the drop by drop addition made it necessary to use a batch process for the preparation of gelatin based nanoparticles.

The invention is based on the realization that the formation of a homogeneous mixture in which the concentration of the organic solvent is high enough results in the formation of nanoparticles by desolvation, and that this is instantaneously achievable by continuously contacting a small amount of the gelatin solution and a small amount of the organic solvent, rather than contacting a small amount of the organic solvent with a large amount of the gelatin solution like in the batch process. Feeding a flow of the gelatin solution and a flow of the organic solvent into a reactor allows the provision of such a homogeneous mixture while avoiding formation of large aggregates.

By the use of the continuous process in a reactor, the gelatin based nanoparticles having a narrow polydispersity index are continuously obtained, advantageously providing an efficient process with a high reproducibility. Unlike the batch process of the prior art in which the results rely on the expertise of the one performing the experiments, the process according to the present invention provides nanoparticles in a reliable manner.

Furthermore, the process according to the present invention allows a high degree of freedom for the parameters of the process. For example, it is possible to adjust the time point at which the crosslinking agent is added. In the batch process, the crosslinking agent must be added after the formation of the non-crosslinked nanoparticles is completed for the whole batch. In comparison, the crosslinking agent can be added as the non-crosslinked nanoparticles are formed according to the process of the present invention.

Surprisingly, it was found that nanoparticles of different controlled sizes can be obtained according to the process of the present invention which are different from the nanoparticles obtained from the same starting compounds by the batch process. In particular, it was found that nanoparticles having an average diameter of up to 800 nm can be obtained by the process according to the present invention.

The mixing efficiency of a reactor is determined by feeding a solution of 0.0319 mol/L KI, 0.0063 mol/L $KIO_3$, 0.0898 mol/L $H_2BO_3^-$ and 0.0898 mol/L NaOH from one inlet and a solution of 0.015 mol/L $H_2SO_4$ to another inlet of the reactor at a volume ratio of 1:1 and measuring the UV absorbance at the outlet of the reactor at 286 nm. A lower number of the mixing efficiency indicates that more mixing took place in the reactor. The method is described more in detail in S. Panić, S. Loebbecke, T. Tuercke, J. Antes, D. Bošković. Experimental approaches to a better understanding of mixing performance of microfluidic devices. Chem. Eng. J. 2004, 101, 409-419.

The inventors have surprisingly found that the suitable range of the sum of the first rate and the second rate for a given reactor to perform the process of the present invention can be determined by performing the Villermaux/Dushman method using the above described solutions. It was found that said suitable range for the sum of the flow rates of the gelatin solution and the organic solvent is the range in which the mixing efficiency for the above described solutions in the reactor is between 0.1 and 1.5. Hence, it can be determined whether a given reactor is suitable for the preparation of the gelatin nanoparticles and the suitable range of the sum of the flow rates can be determined without using the gelatin solution and the organic solvent.

In order to achieve the mixing efficiency of 0.1 and 1.5, the reactor has to have a mixing element. The mixing element in the reactor used in the present invention is arranged in such a way that a mixing efficiency of 0.1 to 1.5 can be achieved by choosing suitable flow rates.

It was found that a too low or too high mixing efficiency results either in the clogging of the channel (no formation of the nanoparticles) or in a high polydistribution index (PDI) of the formed nanoparticles. Preferably, the sum of the first rate and the second rate is chosen such that the reactor has a mixing efficiency as determined by the Villermaux/Dushman method of between 0.25 and 1.3, more preferably between 0.5 and 1.0. In this case, the resulting nanoparticles are small and have low PDI.

It was also found that it is preferable that the mixing starts as soon as possible after the gelatin solution and the organic solvent contact each other. The period from the time point at which the aqueous gelatin solution is fed to the reactor to the time point at which the mixture contacts the mixing element is at most 15 seconds. It was experimentally found that a clogging of the channel occurs when the mixture stays in the channel more than 15 seconds before it is split by the mixing element. Preferably, the period from the time point at which the aqueous gelatin solution is fed to the reactor to the time point at which the mixture contacts the mixing element is 0.01 to 10 seconds. More preferably, the period is 0.1 to 5 seconds.

As used herein, a mixing element is an element which splits a flow into multiple flows and recombines the flows in the reactor. It is possible that the multiple flows are rotated during the split and recombine mixing step. Many types of mixing elements are known. A mixing element typically has repetitive units having the same construction and the split of the flow typically occurs multiple times. The time point at which the mixture contacts the mixing element is understood to mean the time point at which the mixture is split by the mixing element for the first time.

Preferably, the split of the flow occurs at least 10 times, at least 20 times, at least 30 times, at least 40 times, at least 60 times, or at least 80 times. Preferably, the split of the flow occurs at most 300 times, at most 250 times, at most 200 times, at most 150 times, or at most 100 times.

The suitable number of the splits for providing the required mixing efficiency depends e.g. on the flow rates of the inflow and the cross section of the channels of the reactor.

In some preferred embodiments, the mixing element provides at least 60 splits, the mixture flows from the first split to the last split within a period of 60 seconds to 15 minutes and the sum of the first rate and the second rate is 0.4-4.0 mL/min per cross section of the channel in $mm^2$. It was found that these embodiments provide a desirable gelatin based nanoparticles.

As used herein, the term "cross section of the channel" is understood to be an area, A, of the cross section, calculated from a diameter of the channel. Preferably, the cross section of the channel is constant throughout the channel, i.e. when the channel before the split has a cross section of A $mm^2$, each of the channels has a cross section of A $mm^2$ after the split.

The cross section of the channel is preferably 0.1 to 100 $mm^2$, more preferably 0.5 to 5 $mm^2$, more preferably 1 to 3 $mm^2$.

The mixing element is preferably arranged such that the splitting occurs evenly along the channel.

The specific dimensions and structures of suitable mixers and reaction channels for achieving desired mixing may be determined by the skilled person, e.g. as described in US 2006087048, US 2005220915 and WO 2004076056 which describe microreactors for making nanoparticles.

The suspension may be mixed with the solution of the crosslinking agent immediately after the suspension is formed, or may go through a phase in which further nanoparticles are formed, e.g. by passing through further channels.

After the completion of the desolvation, there is an unstable suspension of gelatin-based nanoparticles. This suspension is mixed with a solution of crosslinking agent to stabilize the nanoparticles: free amine groups within gelatin chains of a nanoparticle react with this cross linking agent, thus stabilizing the gelatin chains in the nanoparticles. Preferably, the crosslinking agent is mixed with the suspension at a molar ratio of 0.5:1 to 2:1 between the crosslinking agent and the amine group of the gelatin. More preferably, the cross-linking agent is added in only a slight excess, e.g. at a molar ratio of 1.1:1 to 1.3:1 between the crosslinking agent and the amine group of the gelatin, to prevent interparticle crosslinking: if a large excess of cross-linking agent is added quickly, the agent may crosslink between gelatin chains of two different nanoparticles. The continuous addition of the crosslinking agent to the suspension may be done within the reactor in which the suspension is formed, or outside of the reactor. In either case, the solution of the crosslinking agent is fed with a rate selected to enable appropriate crosslinking without interparticle crosslinking. After the controlled continuous feeding of the crosslinking agent, the resulting mixture is kept outside the mixer. It is to be noted that during the crosslinking reaction, no stirring should be used, as mechanical interaction may result in inter particle aggregation and subsequent inter particle cross linking.

The gelatin solution used in the process according to the invention preferably has a pH value of below 7.0. Preferably, the gelatin solution has a pH of 2-4. This leads to smaller nanoparticles.

The flow rate ratio between the first rate and the second rate is to be chosen depending on the concentrations of the liquids to be fed to the reactor. The amount of the organic solvent with respect to water has to be enough for the particles to be formed. It was found that when the amount of the organic solvent is too small, a clear solution is obtained instead of a suspension of nanoparticles. Preferably, the second rate is higher than the first rate. Accordingly, the ratio of the second rate to the first rate is preferably between 2 and 4. It was found that this range results in a low PDI of the resulting nanoparticles. Most preferably, the ratio of the second rate to the first rate is 2.75 to 3.25 or around 3. It was surprisingly found that the nanoparticle size can be controlled by the ratio between first rate and the second rate when the nanoparticles were formed in a continuous flow reactor, unlike by a batch process where the ratio between the organic solvent and water does not substantially change the nanoparticle size.

The sum of the first rate and the second rate is preferably 0.4-4.0 mL/min per cross section of the channel in $mm^2$.

The aqueous gelatin solution fed to the first mixer may comprise e.g. 0.1 to 25% (w/v) of the gelatin. It was found that a higher concentration leads to a larger particle size. Preferably, the aqueous gelatin solution comprises 0.1 to 18% (w/v), more preferably 1 to 15% (w/v) of the gelatin.

The reaction temperature may vary in a large range as long as the gelatin solution can remain as a solution. Accordingly, the mixer may be maintained at a temperature of e.g. 37° C.-100° C. or 40° C.-70° C.

The solution of the crosslinking agent may comprise e.g. 0.01-1 mol/L of the crosslinking agent, preferably 0.05-0.2 mol/L. The solvent of this solution may be water. Alternatively, a mixture of water and the organic solvent added to the mixer may also be used as the solvent of this solution. This allows adjusting the ratio of the organic solvent to water in the final suspension. The volume ratio of the organic solvent to water may e.g. be 1-5 or 2-4.

In some embodiments, it may be important to determine the feed rate of the solution of the crosslinking agent based on the ratio of the functional groups in the system. Preferably, the solution of the crosslinking agent is fed in step B) such that the ratio of the crosslinking agent to the amine group of the gelatin is 0.5 to 2.0, preferably 1.1 to 1.3.

The ratio of the flow rate of the crosslinking agent to the first rate may be selected depending e.g. on the concentration of the liquids fed to the reactor. Said ratio may e.g. be 0.05-0.3 or 0.1-0.2.

The organic solvent added to the reactor is preferably chosen from the group consisting of methanol, 2-propanol, acetonitrile and acetone. Particularly preferred as the organic solvent is acetone.

The crosslinking agent is preferably chosen from the group consisting of dialdehydes, formaldehyde, isocyanates, diisocyanates, carbodiimides and alkyl dihalides. Particularly preferred as the crosslinking agent is glutaraldehyde.

Pharmaceutically active compounds, e.g. a growth factor may also be added to the system. Hence, the present invention provides a process wherein the gelatin based nanoparticles further comprise a pharmaceutically active compound. In addition to active components for bone regrowth, there are many other applications to functionalized gelatin nanoparticles, such as DNA drug delivery for e.g. gene therapy. Further contemplated applications are drug delivery to kidney and heart. Examples of pharmaceutically active compounds are mentioned in e.g. U.S. Pat. No. 5,932,245, U.S. Pat. No. 5,560,924, WO 2005/000265, which are incorporated herein by reference. For example, in WO 2005/000265, a long list of possible compounds is given: The pharmaceutically active compounds can be selected from a variety of known classes of drugs, including, for example, COX-2 inhibitors, retinoids, anticancer agents, NSAIDS, proteins, peptides, nucleotides, anti-obesity drugs, nutraceuticals, dietary supplements, carotenoids, corticosteroids, elastase inhibitors, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, xanthines, alpha-hydroxy formulations, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, and respiratory illness therapies associated with acquired immune deficiency syndrome. Examples of representative active agents useful in this invention include, but are not limited to, acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, glipizide, irbesartan, ketoconazole, lansoprazole, loratadine, loxapine, mebendazole, mercaptopurine, milrinone lactate, minocycline, mitoxantrone, nelfinavir mesylate, nimodipine, norfloxacin, olanzapine, omeprazole, penciclovir, pimozide, tacolimus, quazepam, raloxifene, rifabutin, rifampin, risperidone, rizatriptan, saquinavir, sertraline, sildenafil, acetyl-sulfisoxazole, temazepam, thiabendazole, thioguanine, trandolapril, triamterene, trimetrexate, troglitazone, trovafloxacin, verapamil, vinblastine sulfate, mycophenolate, atovaquone, atovaquone, proguanil, ceftazidime, cefuroxime, etoposide, terbinafine, thalidomide, fluconazole, amsacrine, dacarbazine, teniposide, and acetyl-salicylate. Exemplary nutraceuticals and dietary supplements are disclosed, for example, in Roberts et al., Nutraceuticals: The Complete Encyclopedia of Supplements, Herbs, Vitamins, and Healing Foods (American Nutraceutical Association, 2001), which is specifically incorporated by reference. A nutraceutical or dietary supplement, also known as phytochemicals or functional foods, is generally any one of a class of dietary supplements, vitamins, minerals, herbs, or healing foods that have medical or pharmaceutical effects on the body. Exemplary nutraceuticals or dietary supplements include, but are not limited to, lutein, folic acid, fatty acids (e. g., DHA and ARA), fruit and vegetable extracts, vitamin and mineral supplements, phosphatidylserine, lipoic acid, melatonin, glucosamine/chondroitin, Aloe Vera, Guggul, glutamin, amino acids (e. g., iso-leucine, leucine, lysine, methionine, phenylanine, threonin, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods." A description of these classes of active agents and a listing of species within each class can be found in Martindale, The Extra Pharmacopoeia, Twenty-ninth Edition (The Pharmaceutical Press, London, 1989), specifically incorporated by reference. The active agents are commercially available and/or can be prepared by techniques known in the art.

The pharmaceutically active components may be added at different stages of the process. For example, the pharmaceutically active compounds may be added to the aqueous gelatin solution and/or the water-miscible organic solvent. In this case, the compounds are incorporated in the nanoparticles as the nanoparticles are formed. Hence, the present invention provides a process in which the aqueous gelatin solution and/or the water-miscible organic solvent comprises the pharmaceutically active compound.

The pharmaceutically active components may also be added after the gelatin solution and the organic solvent are mixed but before the crosslinking agent is added. Hence, the present invention provides a process in which the pharmaceutically active compound is fed to the reactor after the formation of the suspension of the non-crosslinked gelatin based nanoparticles.

The pharmaceutically active components may also be added after the crosslinking agent is added. Hence, the present invention provides a process in which the pharmaceutically active compound is added to the suspension collected from the reactor.

It is possible to feed the pharmaceutically active compounds in a liquid medium separately to the part of the reactor in which the non-crosslinked gelatin based nanoparticles are formed. In this case, the compounds are incorporated in the nanoparticles as the nanoparticles are formed. Feeding the compounds separately is advantageous in that its flow rate can be controlled independently from the aqueous gelatin solution and the water-miscible organic solvent.

It is noted that the invention relates to all possible combinations of features described herein, especially the features recited in the claims.

BRIEF DESCRIPTION OF THE DRAWINGS

The invention will now be explained with reference to the following figures in which.

DETAILED DESCRIPTION OF THE INVENTION

Figure 1:
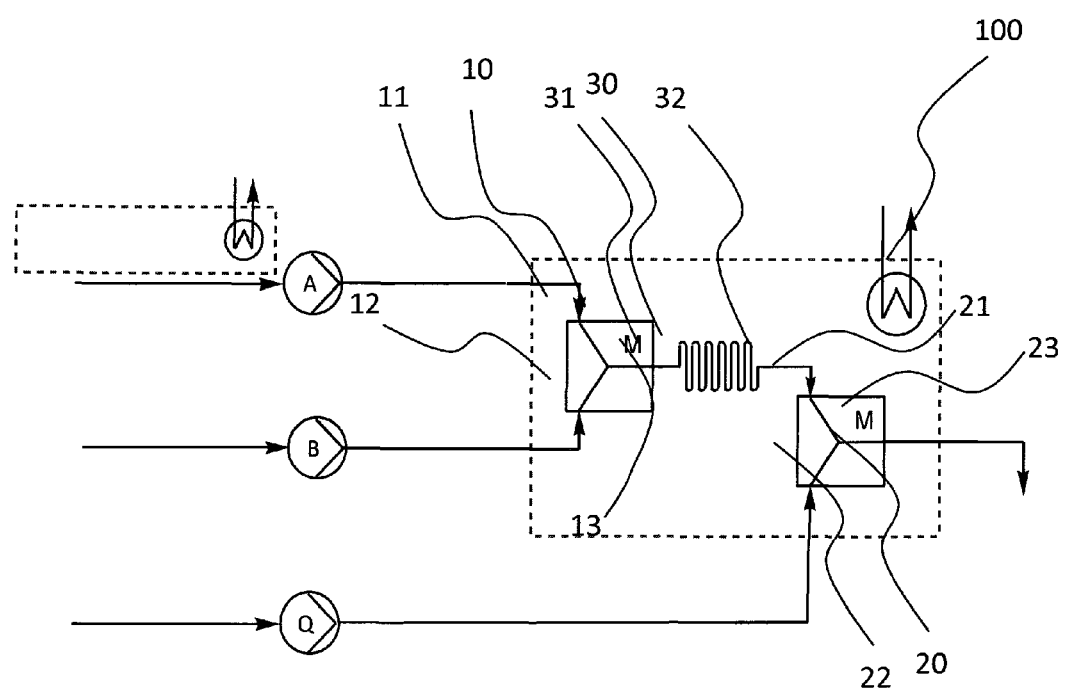
FIG. 1 is a schematic representation of an example of a reactor system used in the process according to the present invention.
Figure 7:
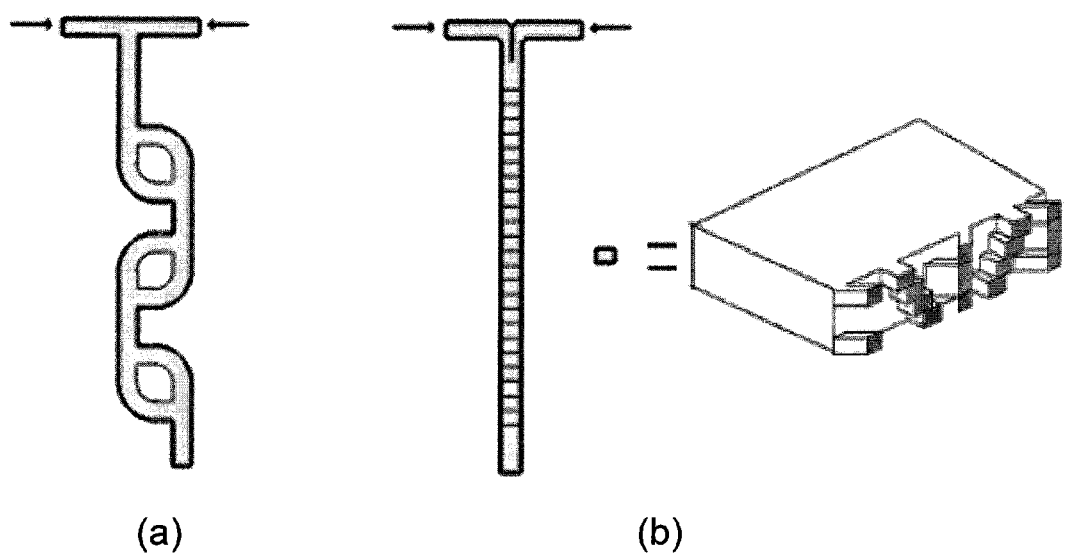

FIG. 1 shows an example of a reactor system for producing gelatin based nanoparticles according to the process of the present invention. The system comprises a reactor 100. The reactor 100 comprises a first mixer 10, a reaction channel 30 and a second mixer 20. The temperature of the reactor is controlled by a temperature controller. The first mixer has a first inlet 11 and a second inlet 12. An aqueous gelatin solution is fed to the first inlet 11 at a controlled rate. The gelatin solution is maintained at a temperature at which the gelatin solution remains liquid. An organic solvent is fed to the second inlet 12 at a controlled rate. The liquids are mixed in the first mixer 10 and flows out from the outlet 13. The mixture enters the reaction channel 30 through its reaction channel inlet 31. By the time the liquid mixture reaches the reaction channel outlet 32, the desolvation process has been completed and a suspension of gelatin based nanoparticles flows at the reaction channel outlet 32. It will be appreciated that the outlet 13 of the first mixer 10 and the reaction channel inlet 31 may not necessarily be clearly distinguishable but rather form one single channel. The first mixer 10 may have the structure as illustrated in FIG. 7.

The suspension from the reaction channel 30 exits from its reaction channel outlet 32 and enters the second mixer through its first inlet 21. A crosslinker solution is also fed to the second mixer 20 through its second inlet 22. The suspension from the first inlet 21 and the crosslinker solution from the second inlet 22 are mixed in the second mixer 20 in which crosslinking of the nanoparticles occur. The crosslinked nanoparticles are collected from the outlet 23.

Many variations of this embodiment is possible. In one variation, a solution or a dispersion of a pharmaceutically active compound is fed to the system. The first mixer 10 or the second mixer 20 may comprise a further inlet through which the pharmaceutically active compound is fed. The microreactor 10 may comprise a further mixer to which the pharmaceutically active compound is fed, which further mixer may be further fed with the liquid from the first microreactor, the reaction channel, or the second microreactor. In this way, gelatin based nanoparticles comprising the pharmaceutically active compound can be formed.

Figure 2:
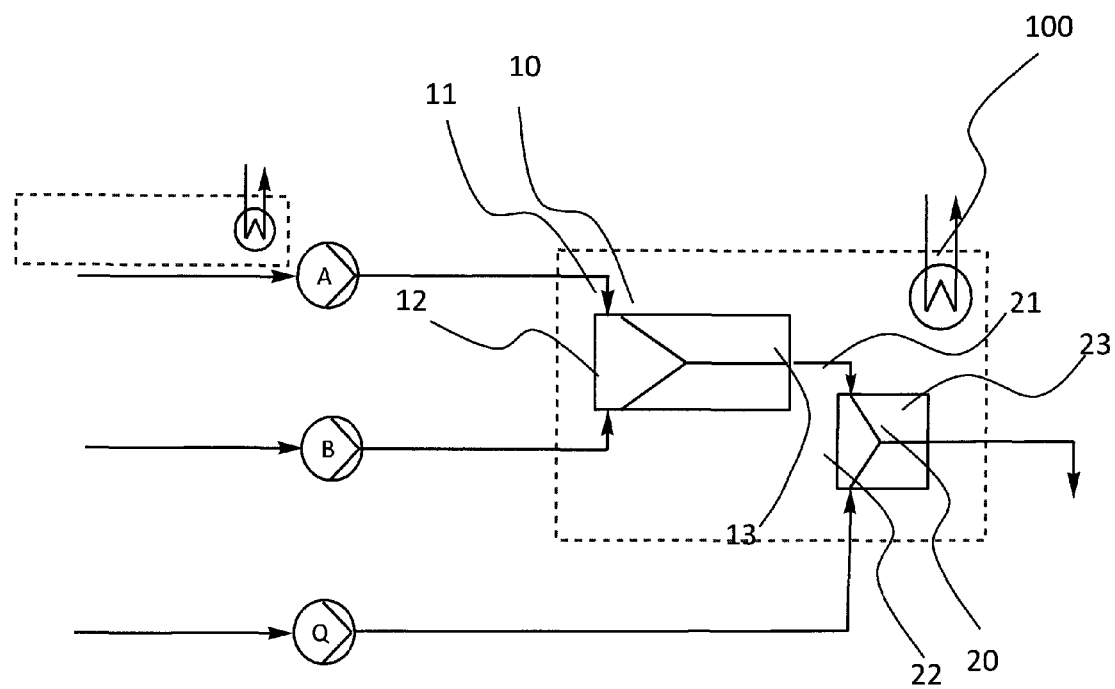
FIG. 2-5 show a schematic representation of various examples of a reactor system used in the process according to the present invention.

FIG. 2 shows a further example of the reactor system for producing gelatin based nanoparticles according to the process of the present invention. This example is the same as in FIG. 1 except that the reactor 100 comprises no reaction channel 30, but the mixer 10 is larger than in FIG. 1 to ensure the extended reaction time for providing the nanoparticles.

Figure 3:
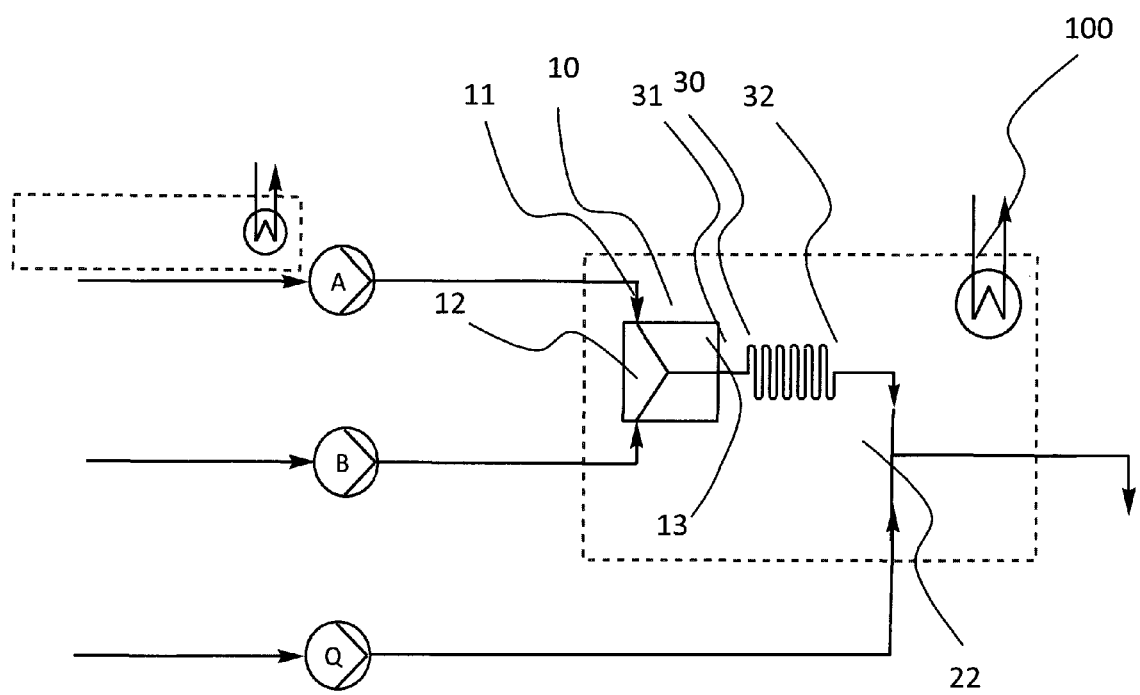

FIG. 3 shows a further example of the reactor system for producing gelatin based nanoparticles according to the process of the present invention. This example is the same as in FIG. 1 except that the reactor 100 does not comprise a second mixer, but a T-splitter is used for the addition of the crosslinking agent.

Figure 4:
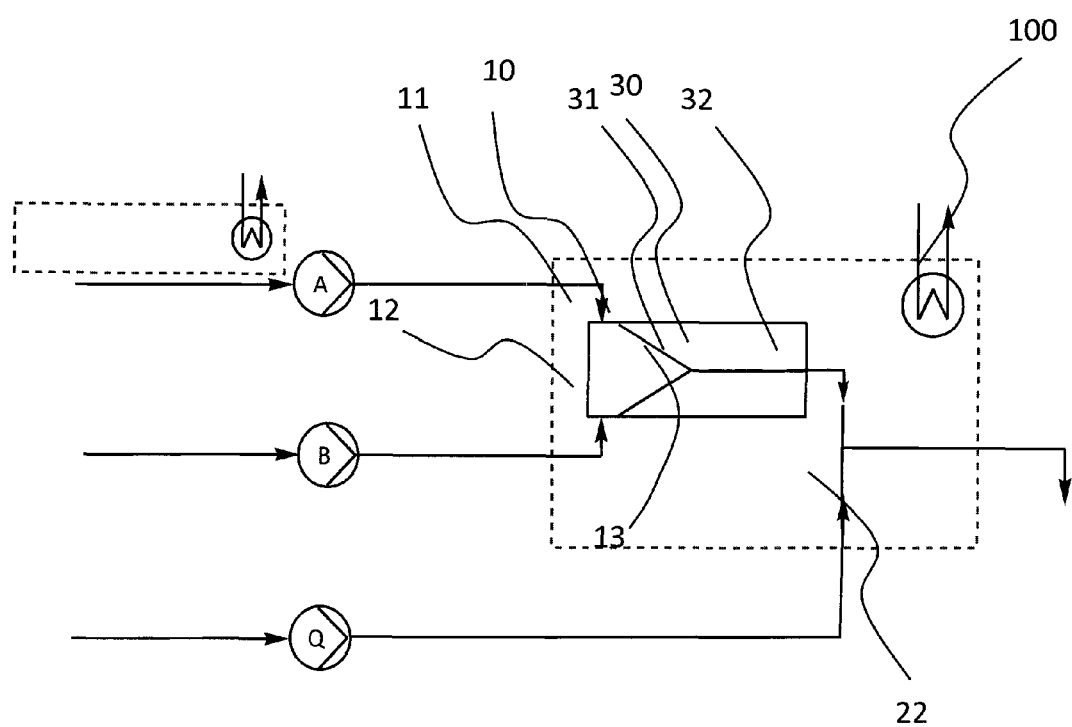

FIG. 4 shows a further example of the reactor system for producing gelatin based nanoparticles according to the process of the present invention. This example is the same as in FIG. 2 except that the reactor 100 does not comprise a second mixer, but a T-splitter is used for the addition of the crosslinking agent.

Figure 5:
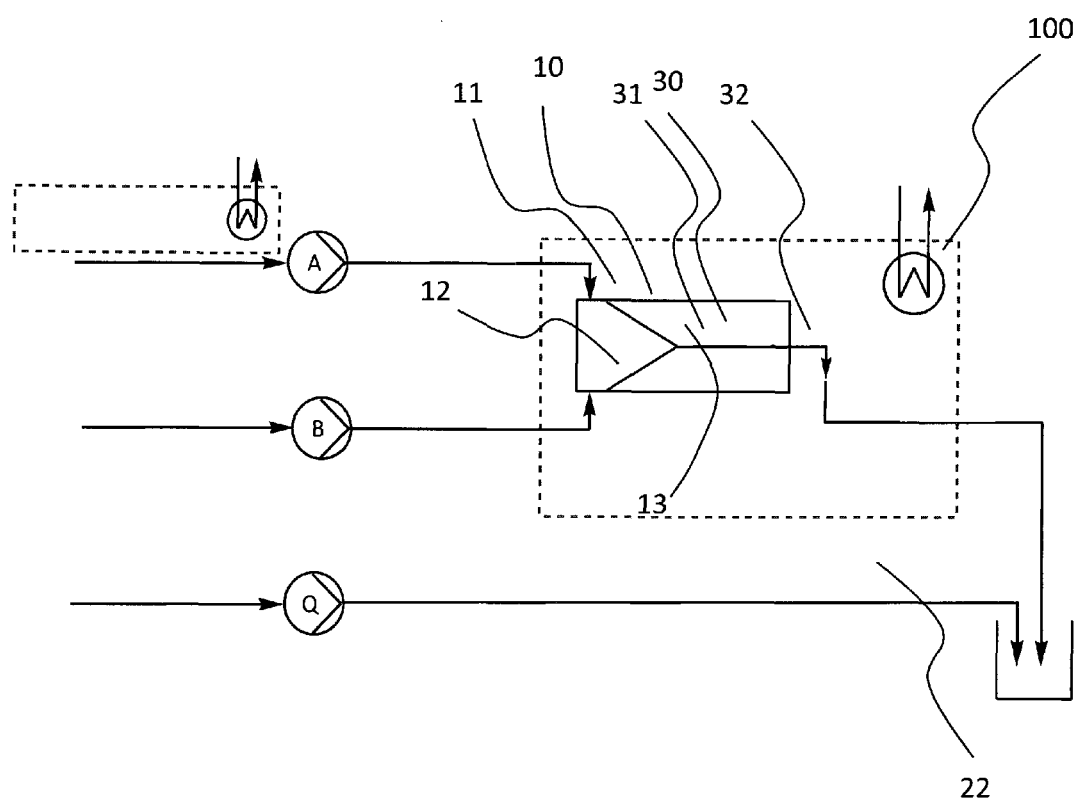

FIG. 5 shows a further example of the reactor system for producing gelatin based nanoparticles according to the process of the present invention. This example is the same as in FIG. 2 except that the reactor 100 does not comprise a second mixer and the crosslinking agent is added outside of the reactor.

Figure 6:
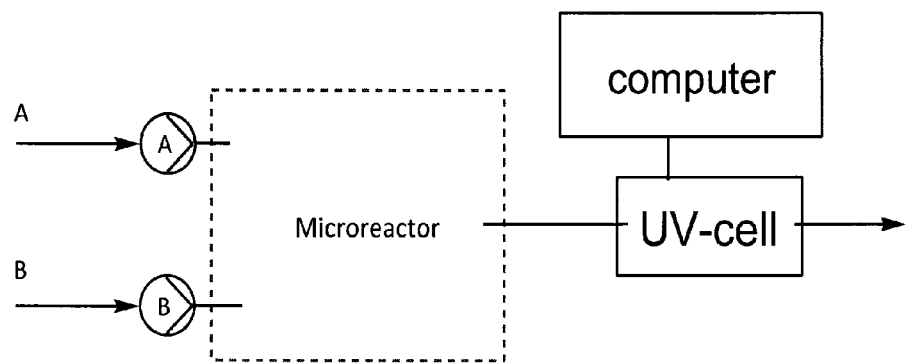
FIG. 6 show a schematic representation of an example of the reactor for the measurement of the Villermaux/Dushman method and FIG. 7 show a schematic representation of examples of a mixing element used in the process according to the present invention.

FIG. 6 shows an example of the reactor system for measuring the mixing efficiency by the Villermaux/Dushman method. In this figure, the outlet of the microreactor is connected to a UV-cell which is coupled to a computer for analyzing the UV absorption. The mixing efficiency of the reactors illustrated in FIG. 1-5 can be determined by setting the flow rate Q to zero and thus making the configuration of FIG. 6.

FIG. 7 shows two examples of a mixing element used in the process according to the present invention. The mixing element of FIG. 7 may be used as the first mixer 10 in FIG. 1-6.

Experiments

Experiments were performed using the following solutions:

Solution A (0.0165 M): Gelatin A from porcine skin (CAS: 9000-70-8)

(5% w/v) in water (pH is adjusted to 2.5)

Solution B: Acetone p.a.

Solution Q (0.1 M): Glutaraldehyde (GTA) (1% w/v) in water/acetone (1:2.57 v/v) Note: solution Q was made by dilution of GTA (25% w/v) in water with water/acetone (1:3 v/v)

The ratio of the crosslinking agent to the amine group of the gelatin was 1.1.

Experiment 1

The reactor system illustrated in FIG. 4 was used. The first mixing unit had a structure as illustrated in FIG. 7(a).

The reactor volume was 2.4 mL. The number of the splits in the reactor was 70. The cross section of the channel was 1.0 mm².

Solution A was kept at an elevated temperature through heating of the stock solution with an isomantle and maintained at 40° C. Solutions A, B and Q were fed to the system at a flow rate as shown in Table 1. The period from the time point at which the flows were fed to the inlets of the reactor and to the time point at which the mixed stream contacted the first splitter is also shown in Table 1.

In each example, the liquid mixture coming out from the reaction channel was a milky suspension, indicating that a suspension of non-crosslinked gelatin based nanoparticles was obtained. In example 1-5, however, the reactor became clogged after a short period of time.

The resulting nanoparticle suspensions were left for 16 hours to let the GTA crosslinking reaction complete. 3 to 4 drops of the solution were diluted to ~1 mL mQ water and analysed with dynamic light scattering (DLS). Thereafter, ~5 ml (approximately equal volume to the suspension) glycine solution (100 mM) was added to block the unreacted GTA. Nanoparticle suspensions were washed 3 times using cycles of centrifugation and re-suspending nanoparticles in purified water sold under the trademark MILLI-Q®. After the third centrifugation, the nanoparticles were resuspended in a mixture of acetone and purified water sold under the trademark MILLI-Q® (1:3) and lyophilized to a dry powder.

TABLE 1

| Example | Flow A | Flow B | Sum of flow rate of A+B | Flow Q | Period Inlet to first split (sec) | Residence time (min) | Size (nm) | PDI |
|---|---|---|---|---|---|---|---|---|
| 1-1 | 0.10 | 0.30 | 0.40 | 0.0165 | 4.25 | 6.00 | 219 | 0.04 |
| 1-2 | 0.20 | 0.60 | 0.80 | 0.033 | 2.13 | 3.00 | 207 | 0.03 |
| 1-3 | 0.40 | 1.20 | 1.60 | 0.066 | 1.06 | 1.50 | 160 | 0.02 |
| 1-4 | 1.00 | 3.00 | 4.00 | 0.165 | 0.43 | 0.60 | 154 | 0.03 |
| 1-5* | 2.00 | 6.00 | 8.00 | 0.33 | 0.21 | 0.30 | 145 | 0.06 |
| 1-6 | 0.20 | 0.60 | 0.80 | 0.033 | 2.13 | 3.00 | 191 | 0.10 |

*After 30 minutes the reactor gets spoiled in this type and size of reactor, due to fouling of the reactor All flow rates are in mL/min. In example 1-6 the Gelatine A (solution A) was exchanged for Gelatine B (bovine skin (CAS: 9000-70-8)). The procedure was identical to the production of nanoparticles from gelatine A.

The mixing efficiency was determined for the sum of the flow rates of A+B used in each example according to the Villermaux/Dushman method using solutions X and Y, as shown in Table 2.

Specifications Solution X and Y

Solution X (in demiwater): 0.0319 mol/L KI 0.0063 mol/L $KIO_3$ 0.0898 mol/L $H_2BO_3^-$ 0.0898 mol/L NaOH Solution Y (in demiwater): 0.015 mol/L $H_2SO_4$ Solution X and Y were pumped through the reactor with a 1:1 flow rate ratio as depicted in Table 2. The temperature of the reactor was 22° C. The outflow of the reactor was directly pumped into the UV-cell (Brand: Avantes, see specifications) to measure UV Absorption at 286 nm (peak height). The reactor and the UV-cell were connected with 1.0 meter tubing with 0.02" I.D. The absorbance measured is equal to the mixing efficiency.

Specifications UV-Cell:

Avantes (Avalight DHc and AvaSpec-ULS3648)

| UV-cell Technical Data | |
|---|---|
| Flow Cell Type | Micro flow Z-cell-1.5 |
| Wavelength Range | 200-2500 nm |
| Optical path length | 1.5 mm |
| Sample volume | 3 µl |
| Tubing OD connection | 1.5 mm (¹/₁₆") |
| Pressure rating | 10 bar |
| Fiber optic coupling | 1.6 mm ferrule |
| Dimensions/material | 32 × 38 × 13 mm/PEEK |

Software

Spectrometer software version 7 for Windows 95/98/2000/NT/ME/XP/Vista for the AvaSpec (AvaSoft 7.5.3)

TABLE 2

| Example | Flow X | Flow Y | Sum of flow rate of X + Y | Mixing efficiency Ab (286 nm) |
|---|---|---|---|---|
| 1-1 | 0.20 | 0.20 | 0.40 | 1.36 |
| 1-2 | 0.40 | 0.40 | 0.80 | 1.01 |
| 1-3 | 0.80 | 0.80 | 1.60 | 0.65 |
| 1-4 | 2.00 | 2.00 | 4.00 | 0.42 |
| 1-5 | 4.00 | 4.00 | 8.00 | 0.21 |
| 1-6 | 0.40 | 0.40 | 0.80 | 1.01 |

For each sum of the flow rate, the mixing efficiency was determined as shown in Table 2. By comparing Tables 1 and 2, it can be seen that the sum of the flow rates of 8.00 which results in the mixing efficiency of more than 0.21 leads to a relatively unstable process for the preparation of the gelatin nanoparticles. Hence, the sum of the flow rates is preferably chosen such that the mixing efficiency is more than 0.21, for example at least 0.25.

Experiment 2

The reactor system illustrated in FIG. 4 was used. The first mixing unit has a structure as illustrated in FIG. 7(b). The second mixing unit did not have a structure for splitting and recombining the flow.

The reactor volume was 3.0 mL. The number of the splits in the reactor was 135. The cross section of the channel was 1.0 mm².

Except for the type of the reactor (different type of splits and reactor volume), the experiment was performed in the same way as in experiment 1.

In each example, the liquid mixture coming out from the reaction channel was a milky suspension, indicating that a suspension of non-crosslinked gelatin based nanoparticles was obtained. Already after the 30$^{th}$ split, the liquid mixture was a milky suspension.

The resulting nanoparticle solutions were treated and analyzed in the same way as in the Experiment 1. Results are shown in Table 3.

TABLE 3

| Example | Flow A | Flow B | Sum of flow rate of A + B | Flow Q | Period Inlet to first split (sec) | Residence time (min) | Size (nm) | PDI |
|---|---|---|---|---|---|---|---|---|
| 2-1 | 0.10 | 0.30 | 0.40 | 0.0165 | 4.45 | 7.50 | 140 | 0.10 |
| 2-2 | 0.20 | 0.60 | 0.80 | 0.033 | 2.22 | 3.75 | 129 | 0.08 |
| 2-3 | 0.50 | 1.50 | 2.00 | 0.0825 | 0.89 | 1.50 | 139 | 0.05 |
| 2-4 | 1.00 | 3.00 | 4.00 | 0.165 | 0.45 | 0.75 | 105 | 0.07 |
| 2-5 | 2.00 | 6.00 | 8.00 | 0.330 | 0.22 | 0.375 | 101 | 0.05 |

Nanoparticle dispersion was obtained by a stable process. It is expected that the mixing efficiency for the reactor used in this experiment for the flow rates as indicated in Table 3 is between 0.1 and 1.5.

TABLE 4

| experiment | scale | Size (nm) | PDI |
|---|---|---|---|
| 3 | 1.25 g | 419 | 0.19 |
| 4 | 12.5 g | 289 | 0.24 |

It can be seen that the size and the PDI of the gelatin nanoparticles substantially differ depending on the scale of the production for the batch process. PDI is found to be very high.

EXAMPLE 5

The reactor system illustrated in FIG. 4 was used. The mixing unit has a structure as illustrated in FIG. 7(a).

Except for the concentration of the gelatin solution, the experiment was performed in the same way as in experiment 1. The concentration of the gelatin solution was varied as indicated in Table 6.

In each example, the liquid mixture coming out from the reaction channel was a milky suspension, indicating that a suspension of non-crosslinked gelatin based nanoparticles was obtained.

The resulting nanoparticle solutions were treated and analyzed in the same way as in the Experiment 1. Results are shown in Table 6.

TABLE 6

| Example | Conc. (%) | Flow A | Flow B | Sum of flow rate of A + B | Flow Q | Period Inlet to first split | Residence time (min) | Size (nm) | PDI |
|---|---|---|---|---|---|---|---|---|---|
| 6-1 | 2.5 | 0.2 | 0.6 | 0.8 | 0.033 | 2.13 | 3.00 | 128 | 0.09 |
| 6-2 | 5 | 0.2 | 0.6 | 0.8 | 0.033 | 2.13 | 3.00 | 207 | 0.03 |
| 6-3 | 7.5 | 0.2 | 0.6 | 0.8 | 0.033 | 2.13 | 3.00 | 216 | 0.03 |
| 6-4 | 10 | 0.2 | 0.6 | 0.8 | 0.033 | 2.13 | 3.00 | 246 | 0.03 |

Experiment 3: Batch Experiment: 1.25 g 1.25 g gelatin A was dissolved into 25 mL purified water sold under the trademark MILLI-Q® at 50° C. Next, 25 mL acetone was added at once and the solution was allowed to cool to room temperature for one hour. The supernatant was discarded and the residue redissolved in 25 ml purified water sold under the trademark MILLI-Q®. The pH was adjusted to 3.0 with addition of 1N HCl. The solution was heated to 50° C. and stirred at 600 rpm. 75 mL of acetone was added with a flowrate of 1.76 mL/min. After addition of the acetone was completed, 4.125 mL Gluteraldehyde was added and the solution was stirred for another 16 hours. 3 to 4 drops of the solution were diluted to ~1 mL mQ water and analysed with dynamic light scattering (DLS).

Experiment 4: Batch Experiment: 12.5 g 12.5 g gelatin A was dissolved into 250 mL purified water sold under the trademark MILLI-Q® at 50° C. Next, 250 mL acetone was added at once and the solution was allowed to cool to room temperature for one hour. The supernatant was discarded and the residue redissolved in 250 mL purified water sold under the trademark MILLI-Q®. The pH was adjusted to 3.0 with addition of 1N HCl. The solution was heated to 50° C. and stirred at 600 rpm. 750 mL of acetone was added with a flowrate of 17.6 mL/min. After addition of the acetone was completed, 41.25 mL Gluteraldehyde was added and the solution was stirred for another 16 hours. 3 to 4 drops of the solution were diluted to ~1 mL mQ water and analysed with dynamic light scattering (DLS).

Example 6-2 is identical to example 1-2.

What is claimed is:

1. A continuous process for the preparation of gelatin based nanoparticles in a reactor comprising a process channel comprising a mixing element therein, the process comprising the following steps:
   A) feeding separately an aqueous gelatin solution at a first rate and a water-miscible organic solvent at a second rate to the process channel of the reactor to be mixed therein, to form a suspension of non-crosslinked gelatin based nanoparticles and
   B) crosslinking the non-crosslinked gelatin based nanoparticles,
   wherein a sum of the first rate and the second rate is chosen such that the reactor has a mixing efficiency as determined by a Villermaux/Dushman method of between 0.1 and 1.5 and
   a period from a time point at which the aqueous gelatin solution is fed to the reactor to a later, second time point at which the mixture of the aqueous gelatin solution and the organic solvent contacts the mixing element is at most 15 seconds.

2. The process according to claim 1, wherein the sum of the first rate and the second rate is chosen such that the process has a mixing efficiency as determined by the Villermaux/Dushman method of between 0.25 and 1.3.

3. The process according to claim 1, wherein the period from the time point at which the aqueous gelatin solution is fed to the reactor to the time point at which the mixture contacts the mixer is 0.01 seconds to 10 seconds.

4. The process according to claim 1, wherein the aqueous gelatin solution comprises 0.1 to 18% (w/v) of the gelatin.

5. The process according to claim 1, wherein a solution of a crosslinking agent is fed in step B) such that a ratio of the crosslinking agent to an amine group of the gelatin is 0.5 to 2.0.

6. The process according to claim 1, wherein the ratio of the second rate to the first rate is between 2 to 4.

7. The process according to claim 1, wherein a cross section of the process channel is 0.5 mm$^2$ to 5 mm$^2$.

8. The process according to claim 1, wherein the mixing element provides at least 10 times of a split of the flow.

9. The process according to claim 1, wherein the sum of the first rate and the second rate is 0.4 mL/min to 4.0 mL/min per cross section of the channel in mm$^2$.

10. The process according to claim 1, wherein the aqueous gelatin solution has a pH of 2 to 4.

11. The process according to claim 1, wherein the organic solvent is one or more of methanol, 2-propanol, acetonitrile and acetone.

12. The process according to claim 1, wherein the crosslinking agent is one or more of dialdehydes, formaldehyde, isocyanates, diisocyanates, carbodiimides and alkyl dihalides.

13. The process according to claim 1, wherein the gelatin based nanoparticles further comprise a pharmaceutically active compound.

14. The process according to claim 13, wherein the aqueous gelatin solution and/or the water-miscible organic solvent comprises the pharmaceutically active compound.

15. The process according to claim 14, wherein the pharmaceutically active compound is fed to the reactor after the formation of the suspension of the non-crosslinked gelatin based nanoparticles.

16. The process according to claim 2, wherein the period from the time point at which the aqueous gelatin solution is fed to the reactor to the time point at which the mixture contacts the mixer is 0.01 seconds to 10 seconds, wherein the aqueous gelatin solution comprises 0.1 to 18% (w/v) of the gelatin, wherein a solution of a crosslinking agent is fed in step B) such that a ratio of the crosslinking agent to an amine group of the gelatin is 0.5 to 2.0, and wherein the ratio of the second rate to the first rate is between 2 to 4.

17. The process according to claim 16, wherein a cross section of the process channel is 0.5 mm$^2$ to 5 mm$^2$, wherein the mixing element provides at least 10 times of a split of the flow, wherein the sum of the first rate and the second rate is 0.4 mL/min to 4.0 mL/min per cross section of the channel in mm$^2$, and wherein the aqueous gelatin solution has a pH of 2 to 4.

18. The process according to claim 17, wherein the organic solvent is one or more of methanol, 2-propanol, acetonitrile and acetone, wherein the crosslinking agent is one or more of dialdehydes, formaldehyde, isocyanates, diisocyanates, carbodiimides and alkyl dihalides, and wherein the gelatin based nanoparticles further comprise a pharmaceutically active compound.

19. The process according to claim 1, wherein the sum of the first rate and the second rate is chosen such that the process has a mixing efficiency as determined by the Villermaux/Dushman method of between 0.5 and 1.0, wherein a solution of a crosslinking agent is fed in step B) such that the ratio of the crosslinking agent to an amine group of the gelatin is 1.1 to 1.3, wherein the ratio of the second rate to the first rate is between 2.75 and 3.25, and wherein a cross section of the process channel is 1 mm$^2$ to 3 mm$^2$.

20. The process according to claim 18, wherein the sum of the first rate and the second rate is chosen such that the process has a mixing efficiency as determined by the Villermaux/Dushman method of between 0.5 and 1.0, wherein a solution of a crosslinking agent is fed in step B) such that the ratio of the crosslinking agent to an amine group of the gelatin is 1.1 to 1.3, wherein the ratio of the second rate to the first rate is between 2.75 and 3.25, and wherein a cross section of the process channel is 1 mm$^2$ to 3 mm$^2$.

* * * * *